United States Patent
Rydberg

(10) Patent No.: US 6,685,894 B1
(45) Date of Patent: Feb. 3, 2004

(54) AIR FLOW DISTRIBUTION MEANS

(75) Inventor: Carl-Magnus Rydberg, Halmstad (SE)

(73) Assignee: Getinge Sterilization Aktiebolag, Getinge (SE)

(*) Notice: Subject to any disclaimer, the term of this patent is extended or adjusted under 35 U.S.C. 154(b) by 0 days.

(21) Appl. No.: 09/959,277
(22) PCT Filed: Apr. 27, 2000
(86) PCT No.: PCT/SE00/00793
§ 371 (c)(1), (2), (4) Date: Oct. 19, 2001
(87) PCT Pub. No.: WO00/64494
PCT Pub. Date: Nov. 2, 2000

(30) Foreign Application Priority Data

Apr. 27, 1999 (SE) .............................. 9901497

(51) Int. Cl.7 .................................. A61L 2/06
(52) U.S. Cl. ..................................... 422/292
(58) Field of Search ........................ 422/292

(56) References Cited

U.S. PATENT DOCUMENTS 4,576,792 A   3/1986   Mårtensson
5,178,841 A   1/1993   Vokins et al.

FOREIGN PATENT DOCUMENTS

DE   38 00 181 A1   7/1989
DE   198 20 343 A1   7/1999

Primary Examiner—Hoa Van Le
(74) Attorney, Agent, or Firm—Burns, Doane, Swecker & Mathis, L.L.P.

(57) ABSTRACT

This invention relates to a gaseous medium flow distribution means for use in or in connection to a sterilizer chamber of the type in which a gaseous medium, such as steam or air, is brought to circulate. The means comprises cover means covering essentially a section area of said chamber, and said cover means are defining slits through which air is allowed to pass, said slits being shaped and distributed over the area so as to control the air flow inside said chamber in a predetermined manner.

20 Claims, 5 Drawing Sheets

AIR FLOW DISTRIBUTION MEANS

TECHNICAL FIELD OF THE INVENTION

The present invention relates to a gaseous flow distribution means for use in or in connection to a sterilizer chamber of the type in which a gaseous medium, such as steam or air, is brought to circulate.

BACKGROUND ART

Sterilizers for heat treatment of various articles, which articles are placed in a chamber in a pressure vessel, are widely used for sterilising objects both in pharmaceutical industry and for hospital or other similar use. One such arrangement for sterilising is described in U.S. Pat. No. 4,576,792.

In a chamber in a pressure vessel, e g an autoclave, articles are heat treated by water, which is sprayed over the articles through nozzles and which supplies heat to or removes heat from the articles. Simultaneously, a gaseous medium, e g a mixture of steam and air, is forced by an impeller to flow through the articles in countercurrent to the water.

Since the temperature of the articles is critical to ensure a successful sterilisation, the need of even temperature distribution in the chamber is well known.

In an autoclave as the one set out in U.S. Pat. No. 4,576,792, there are at least two problems involved that makes the temperature throughout the chamber unevenly distributed.

Primary, the flow of gaseous medium that is forced to flow through the articles, does not have the same intensity throughout the chamber. This problem is of course also occurring in sterilizers of the kind using only a gaseous medium, and no liquid, for sterilising. The variations in the flow of the gaseous medium will cause an uneven temperature distribution both between different articles and within one article. This is a considerable problem, especially when dealing with articles that are sensitive to being heated during longer periods of time, such as certain biologically active materials. To ensure that all articles are sterilised, the procedure will have to continue for a certain period of time that is adapted to the articles being least exposed to heat, which will risk to cause damage to those articles that are mostly exposed to the heat.

Secondly, the liquid flow is not constant through the chamber, or even in one cross-sectional area of the chamber. This is due to the fact that the nozzles, which are normally provided in the top of the chamber, spread liquid in a cone-like shape from the outlet of the nozzles. The liquid is thus not homogeneously brought over the articles to be sterilised. Instead, certain zones of articles or parts of one article obtain different temperatures due to the uneven distribution of liquid. Much liquid is also spread to the walls of the chamber, where it does not contribute to the sterilisation procedure. Also, the nozzles are rather expensive.

SUMMARY OF THE INVENTION

The present invention solves the first problem as set out above by providing a gaseous flow distribution means according to the preamble, characterised in cover means covering essentially a section area of said chamber, said area being disposed in an angle to the flow of gaseous medium. Said cover means are further defining slits, through which gaseous medium is allowed to pass. Said slits are shaped and distributed over the area so as to control the gaseous flow inside said chamber in a predetermined manner.

In that the slits are distributed over the area of the chamber, the gaseous medium can pass through slits in certain chosen parts of the area, which provides a means for controlling the gaseous flow. In prior art techniques, a fan device usually circulates the air, with a suction inlet provided opposing the fan, and air outlets close to the periphery of the chamber walls, said outlets opposing the suction inlet so as to provide a flow throughout the chamber. The gaseous flow is however not further controlled.

With an appropriate shaping and distribution of the slits in said plate a laminar gaseous flow can for example be provided. Such a flow has an advantage in being evenly distributed in the sterilizer chamber and thereby improving the homogeneity of the heat distribution inside the chamber.

To create such a flow, said means could advantageously be arranged adjacent to a suction out- or inlet of a fan device for circulating said air in said sterilizer chamber. Thus the direction of the flow is instantly affected by the control means.

Advantageously, the total of the open areas of said slits corresponds generally to the area of said suction out- or inlet. This is to prevent pressure differences between different sections of the chamber.

Preferably, slits are provided in regions that are not directly opposing said suction out- or inlet. This is to ensure the desired gaseous distribution effect.

At least one slit could of course be provided opposing said suction out- or inlet.

Advantageously, a plate in which the slits are cut out can constitute said means. The plate would then be provided in the sterilizer chamber. Such a plate is relatively easily manufactured and handled, and could also be formed as an extra equipment for insertion in existing sterilizers.

The second problem mentioned in the previous paragraph is solved by a gaseous flow distribution means according to the preamble, being formed by a plate, which is provided with an outermost frame. The plate is further perforated for allowing water passage through the cover means of the plate. The slits as previously described are provided with edges that are extending longitudinally above said frame, so that air passage through said slits are possible even when the plate is filled with liquid.

Such a means is unique in allowing a circulating gaseous flow and at the same time providing an even water distribution through the perforations of the plate. The gaseous flow though the slits is ensured by the slits being provided with edges that extend longitudinally above said frame of the plate. The maximum water level of the plate will of course be limited to the height of the frame, and thus no water will obstruct the slits and then impact on the gaseous medium circulation.

By such a means, an even water (or any other liquid) distribution is realised by the perforations, and an even, preferably laminar gaseous flow is realised by the slits. The plate thus solves the two above-mentioned problems efficiently and in an easy realisable manner.

DETAILED DESCRIPTION OF PREFERRED EMBODIMENTS OF THE INVENTION

Figure 1:
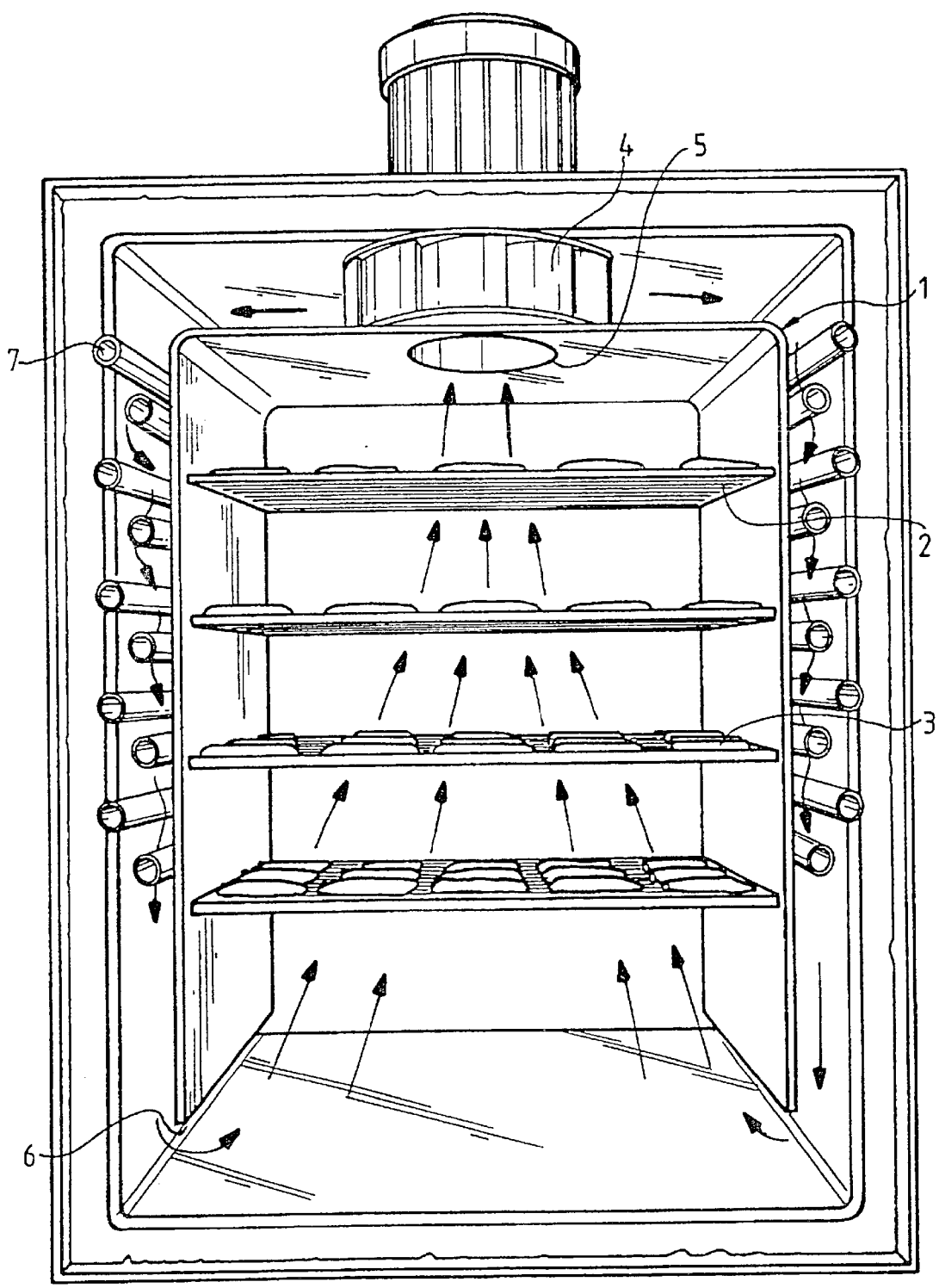
FIG. 1 is a prior art embodiment of a sterilizer using a gaseous medium for sterilising.

FIG. 1 shows an embodiment of a sterilizer according to prior art in which only gaseous medium is used for sterilising. The sterilisation chamber 1 contains several shelves 2 on which bags 3 with a content that are to be sterilised are disposed. The gaseous medium is brought into circulation in the chamber 1 by a fan device 4. The fan suction inlet 5 is provided in the roof of the chamber 1. The outlet 6 for the gaseous medium is provided at the bottom of the chamber 1. In the walls of the chamber 1 where the gaseous medium pass there are heating/cooling elements 7 for heating or cooling the gaseous medium, according to the sterilising process to be proceeded. The gaseous medium thus enters in the chamber 1 close to the chamber walls through the outlet 6. The medium is then sucked out of the chamber through an opening in the centre of the chamber roof, the suction inlet 5, opposing the fan device 4. The resulting gaseous flow will thus roughly follow a way as set out by the arrows in FIG. 1, that is from the walls of the chamber 1 towards the centre, when moving upwards in the chamber 1. The distribution of the gaseous flow is obviously not homogeneous.

Figure 2:
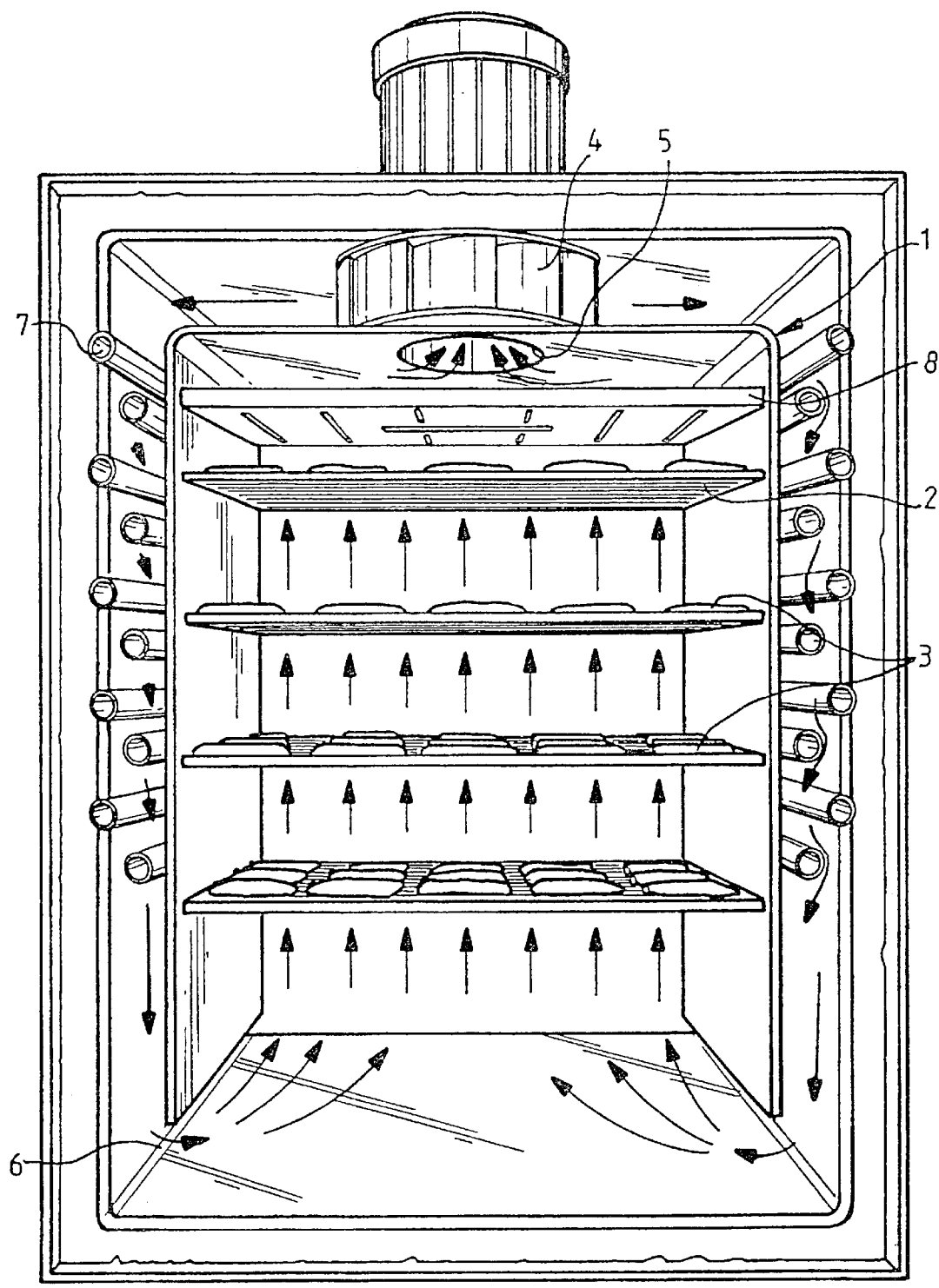
FIG. 2 shows the sterilizer of FIG. 1 with a gaseous flow distribution means according to the invention.

In FIG. 2 the same sterilizer as in FIG. 1 is shown, but being provided with a means 8 according to the invention in front of the suction inlet 5 of the fan 4. Gaseous medium will thus be sucked into the chamber walls from different parts of the cross sectional area of the chamber 1, which, as seen by the arrows indicating the flow, will make the flow tend to a more laminar and thus more homogeneous profile.

Figure 3:
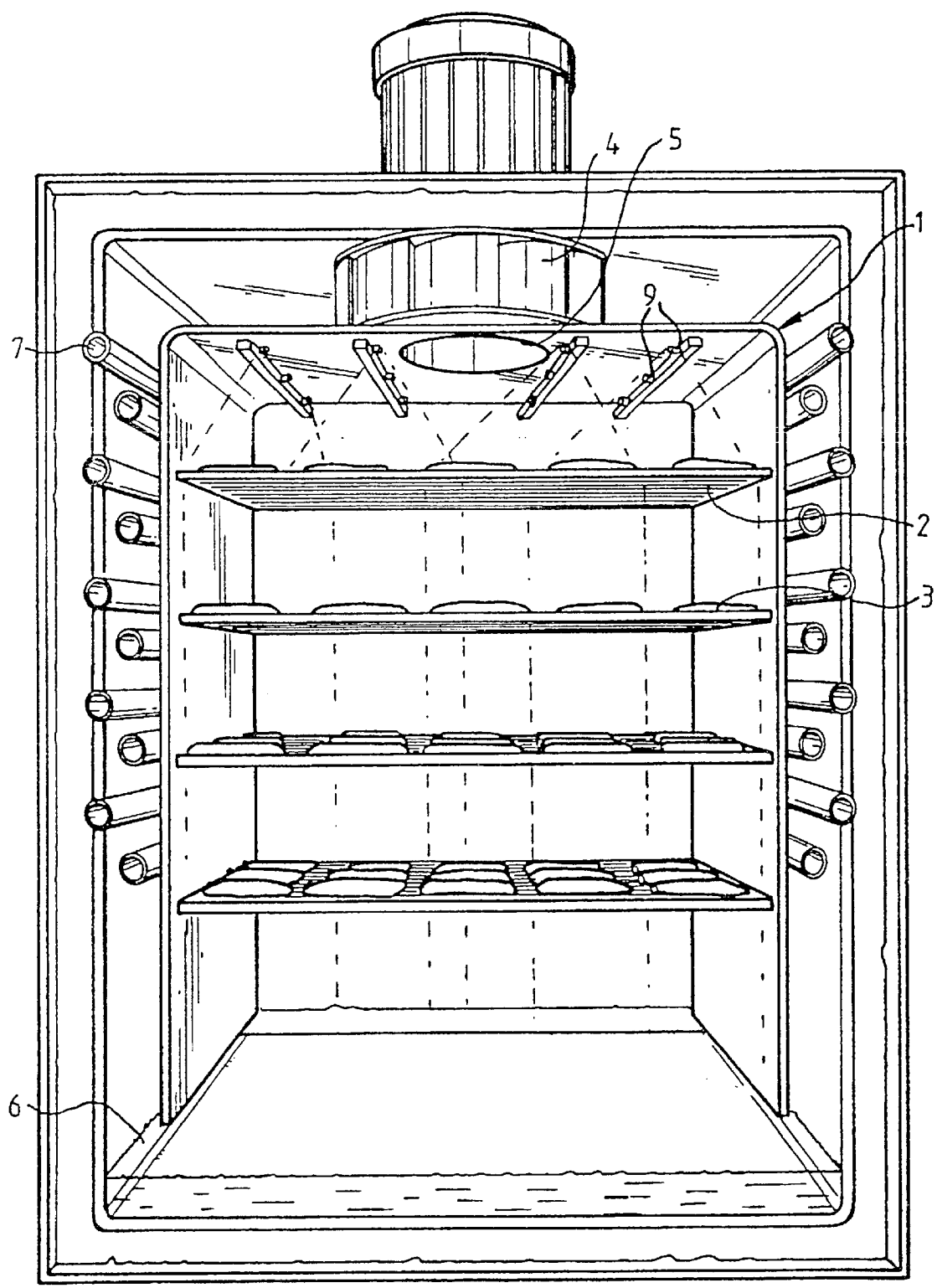
FIG. 3 is a prior art embodiment of a sterilizer using both liquid and gaseous medium for sterilising.

In FIG. 3 a sterilizer resembling to the sterilizer shown in FIG. 1 is shown, apart from that this sterilizer does also use liquid for sterilising articles. The liquid, usually water, is then provided through the nozzles 9 in the roof of the sterilising chamber. The liquid sprinkling from the nozzles is sometimes used simultaneously with the gaseous circulation. The nozzles 9 have the disadvantage of distributing the liquid unevenly and especially they sprinkle a rather great amount of liquid onto the sterilizer walls where it does not contribute as desired to the sterilising process. Besides, such nozzles 9 are rather expensive. The air flow, as indicated by the arrows, is the same as for the sterilizer of FIG. 1.

Figure 4:
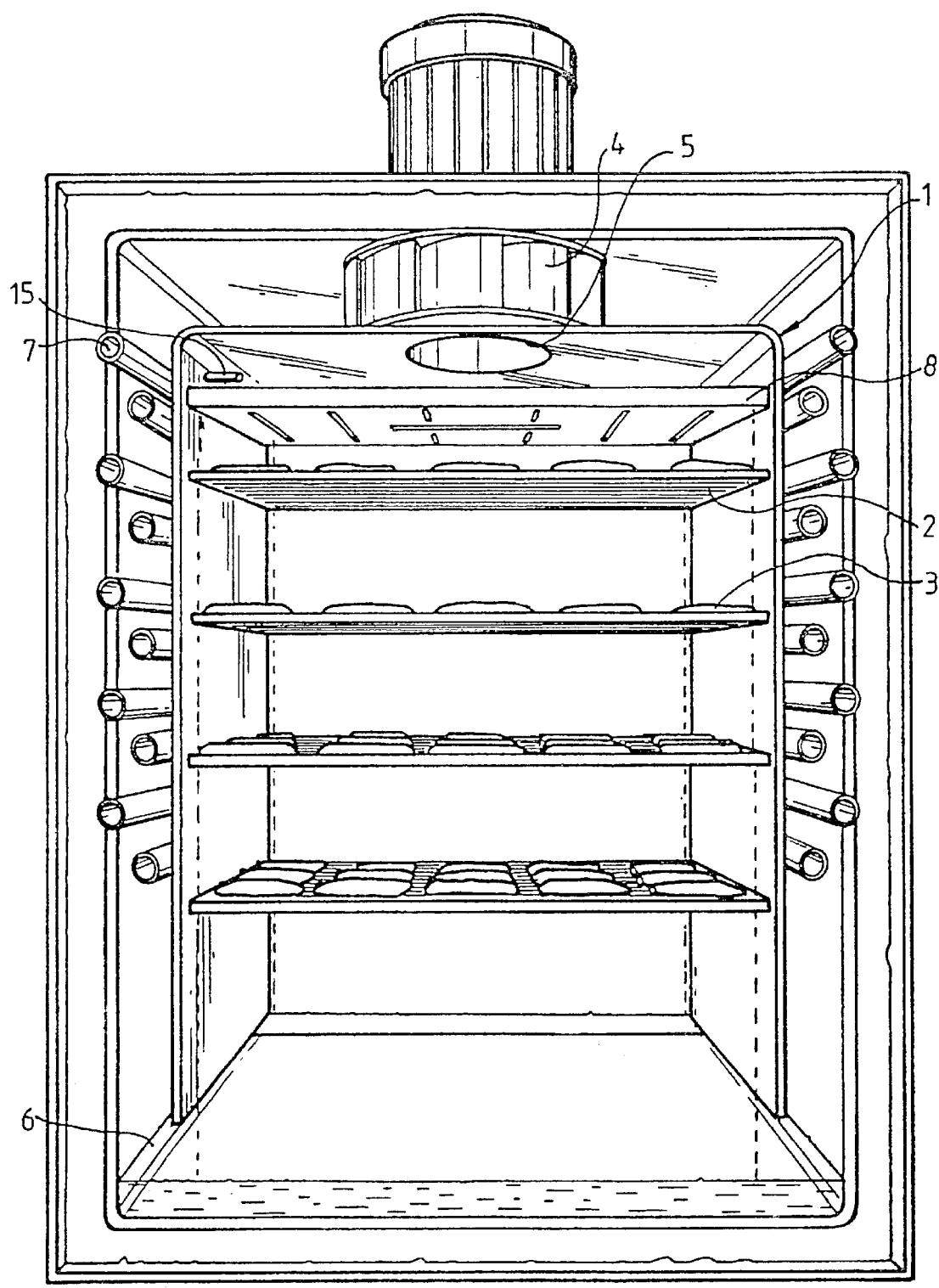
FIG. 4 shows the sterilizer of FIG. 3 with a gaseous flow distribution means according to the invention.
Figure 5:
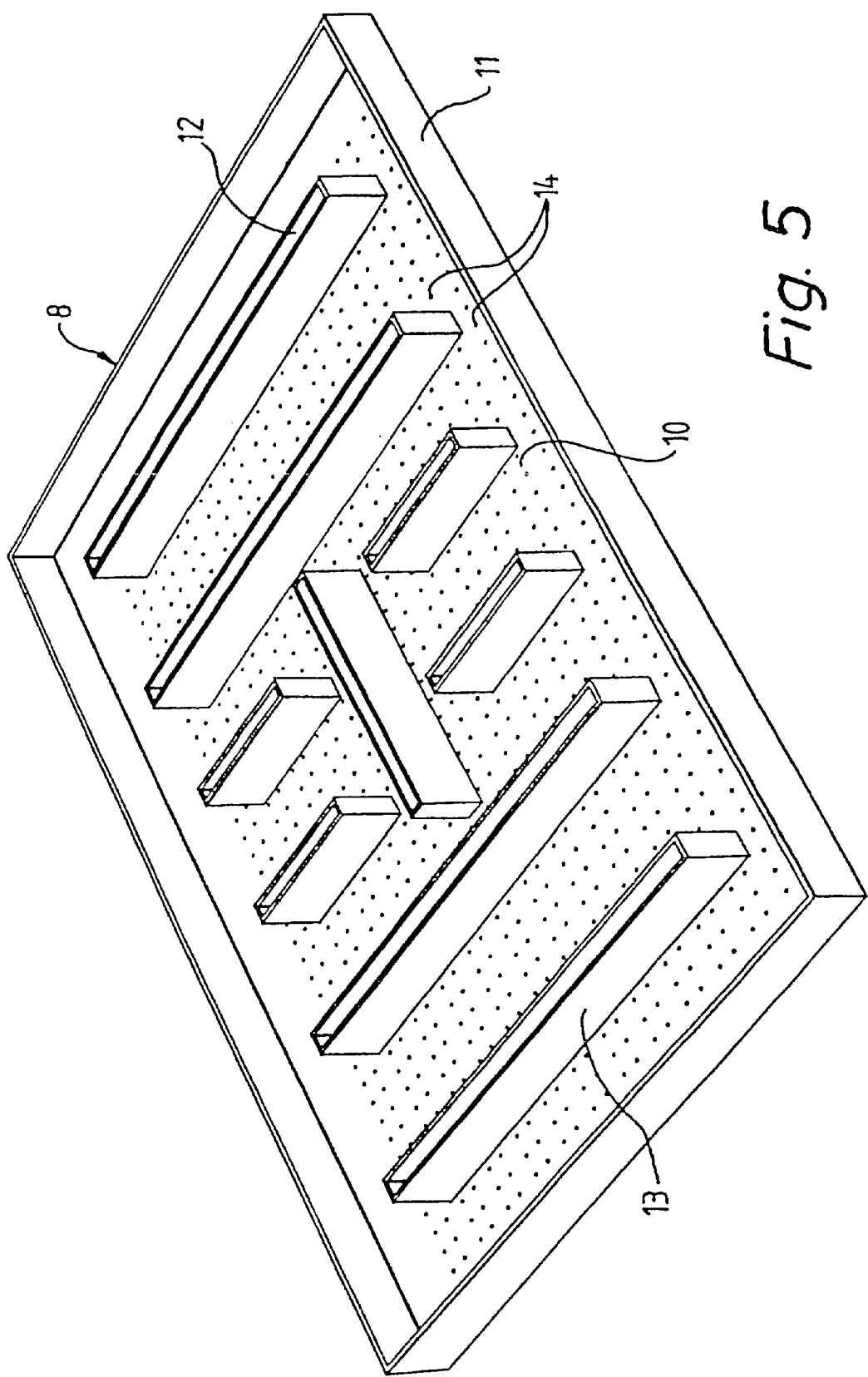
FIG. 5 shows an embodiment of the gaseous flow distribution means according to the invention.

In FIG. 4 a sterilizer ressembling to the one of FIG. 3 is shown, apart from that in the steriliser of FIG. 4, the nozzles 9 are excluded and instead a common water inlet 15 is used. The sterilizer is furter provided with a means 8 according to the invention, which is disposed adjacent to the suction inlet 5 of the fan device 4. The means 8 consist of a plate 10 being provided with a surrounding frame 11. (FIG. 5.) The plate 10 is further provided with slits 12 for passage of the gaseous medium. Each slit 12 is provided with edges 13 that extend longitudinally over the frame 11 of the plate 10. The frame 11 defines the highest possible water level on the plate 10, since excessive water will simply flow over the frame 11. With the edges 13 of the slits 12 protruding over the maximal water level one is sure to always keep the slits 12 open for passage of gaseous medium. The plate 10 is further provided with perforations 13 for passage of the liquid used. These perforations 13 makes the liquid "rain" down into the chamber in an evenly distributed way, as compared to the liquid sprinkled out of the nozzles 9 of the sterilizer of FIG. 3. The water supplied from the water inlet 15, can preferably be supplied in such amount so that excessive water will flow over the frame 11 all of the process time. Thus, an even distribution of water over the area of the plate 10 is ensured.

For ensuring good circulation of the gaseous medium, it is important not to place the plate 10 to close to the suction inlet 5, which would delimit the efficiency of the fan 4. The suction can also be helped by the arrangement of baffles adjacent to the fan device 4, said baffles leading the gaseous medium to the suction inlet 5, and preventing the outcome of turbulent regions between plate 10 and fan 4 where the gaseous medium is not properly circulated.

It is also important to shape and distribute the slits 12 in such a way, that the edges 13 of the slits will not form a closed area in which the liquid can be captured. Such an area would, if it do not have any contact with the frame 11 of the plate 10, be a potential area for liquid build up.

It is of course possible to realise many different kinds of means according to the invention, and still remain within the scope of this invention. It might for example be possible not to use a plate 10 as the base for building the means according to the invention. For example, the cover means could be made out by partly overlapping smaller plates, where the overlapping parts will constitute the desired slits 12.

The placement of the means according to the invention is not limited to the upper part of a sterilisation chamber 1 as shown in the examples above. Two means, one at the end of the suction inlet 5, and the other at the end of a blow out outlet 6, would probably provide good controlling properties. Means according to the invention can of course also be placed inside of the chamber, not in the close neighbourhood of any of the ends of the chamber 1, all depending on which kind of flow distribution that is desired. If a gaseous medium suction inlet 4 or blow out outlet 6 is provided at a side wall of the chamber 1, it would naturally be efficient to place the means according to the invention so as to control the horizontal flow, in the same way as a longitudinal flow is controlled in the described embodiments.

If the flow of gaseous medium is provided perpendicular to the flow of liquid, it is possible to use a means according to the invention only to control the flow of the gaseous medium. The flow of liquid could of course be made more homogeneous by using a simple perforated plate, without any slits for gaseous medium passage.

The shape and placement of the slits 12 could be varied in a many ways.

What is claimed is:

1. Gaseous medium flow distribution means for use in or in connection to a sterilizer chamber (1) of the type in which a gaseous medium, such as steam or air, is brought to circulate, characterised in cover means (10) covering essentially a section area of said chamber (1), said area being disposed at an angle to the flow of gaseous medium, said cover means (10) defining slits (12), through which the gaseous medium is allowed to pass, said slits (12) being shaped and distributed over the area so as to control the air flow inside said chamber (1) in a predetermined manner, whereby said cover means (10) is provided with an outermost frame (11), and also is provided with perforations (14) for allowing water passage through the cover means (10), and said slits (12) is provided with edges (13) extending longitudinally above said frame (11), so that air passage through said slits (12) is possible even when the plate (10) is filled with liquid.

2. Gaseous medium flow distribution means according to claim 1, characterised in said slits (12) being shaped and distributed over the area so as to create a generally laminar gaseous medium flow inside the chamber (1).

3. Gaseous medium flow distribution means according to claim 1, characterised in said means being arranged adjacent to a suction out- (6) or inlet (5) of a circulation device (4) for circulating said gaseous medium in said sterilizer chamber (1).

4. Gaseous medium flow distribution means according to claim 1, characterised in that the total of the open areas of said slits (12) corresponds generally to the area of said suction out- (6) or inlet (5).

5. Gaseous medium flow distribution means according to claim 1, characterised in that slits (12) are provided in regions that are not directly opposing said suction out- (6) or inlet (5).

6. Gaseous medium flow distribution means according to claim 1, characterised in that at least one slit (12) is provided opposing to said suction out- or inlet (6, 5).

7. Gaseous medium flow distribution means according to claim 1, characterised in said cover means being constituted by a plate (10) in which the slits (12) are cut out.

8. Gaseous medium flow distribution means according to claim 1, characterised in said means being provided so as not to disturb the general circulation of gaseous medium.

9. Gaseous medium flow distribution means according to claim 8, characterised in said means being provided at least a predetermined distance from the suction in- or outlet (5, 6) of the circulation.

10. Gaseous medium flow distribution means according to claim 1, characterised in that at least one baffle is provided at or adjacent to said circulation device (4) to enhance circulation.

11. Gaseous medium flow distribution means according to claim 1, characterised in the slits (12) being provided so as to prevent water stocking on the plate by providing liquid run through areas between the edges (13) of the different slits (12).

12. Gaseous medium flow distribution means according to claim 2, characterised in said means being arranged adjacent to a suction out- (6) or inlet (5) of a circulation device (4) for circulating said gaseous medium in said sterilizer chamber (1).

13. Gaseous medium flow distribution means according to claim 2, characterised in that the total of the open areas of said slits (12) corresponds generally to the area of said suction out- (6) or inlet (5).

14. Gaseous medium flow distribution means according to claim 3, characterised in that the total of the open areas of said slits (12) corresponds generally to the area of said suction out- (6) or inlet (5).

15. Gaseous medium flow distribution means according to claim 2, characterised in that slits (12) are provided in regions that are not directly opposing said suction out- (6) or inlet (5).

16. Gaseous medium flow distribution means according to claim 2, characterised in that at least one slit (12) is provided opposing to said suction out- or inlet (6, 5).

17. Gaseous medium flow distribution means according to claim 2, characterised in said cover means being constituted by a plate (10) in which the slits (12) are cut out.

18. Gaseous medium flow distribution means according to claim 2, characterised in said means being provided so as not to disturb the general circulation of gaseous medium.

19. Gaseous medium flow distribution means according to claim 2, characterised in that at least one baffle is provided at or adjacent to said circulation device (4) to enhance circulation.

20. Gaseous medium flow distribution means according to claim 2, characterised in the slits (12) being provided so as to prevent water stocking on the plate by providing liquid run through areas between the edges (13) of the different slits (12).

\* \* \* \* \*